United States Patent [19]

Schouteeten et al.

[11] Patent Number: 4,518,800
[45] Date of Patent: May 21, 1985

[54] PROCESS FOR PREPARATION OF CRYSTALLIZED MONOHYDRATED SODIUM PHENYLPYRUVATE

[75] Inventors: Alain Schouteeten, Ezanville; Yani Christidis, Paris, both of France

[73] Assignee: Societe Francaise Hoechst, Puteaux, France

[21] Appl. No.: 630,427

[22] Filed: Jul. 13, 1984

[30] Foreign Application Priority Data

Jul. 18, 1983 [FR] France ................... 83 11792

[51] Int. Cl.³ ............................................. C07C 59/84
[52] U.S. Cl. .................................................. 562/459
[58] Field of Search ......................................... 562/459

[56] References Cited

U.S. PATENT DOCUMENTS

| | | | |
|---|---|---|---|
| 3,254,109 | 3/1966 | Hartle | 562/459 |
| 3,412,116 | 11/1968 | Reinheckel et al. | 562/459 |
| 3,855,245 | 12/1974 | Koyama et al. | 562/459 |
| 4,042,617 | 8/1977 | Kogure et al. | 562/459 |
| 4,334,089 | 6/1982 | Kraas et al. | 562/459 |

FOREIGN PATENT DOCUMENTS

WO81/01285  5/1981  PCT Int'l Appl. ............... 562/459

OTHER PUBLICATIONS

Journal of the Chemical Society Chemical Communications, No. 24, Dec. 20, 1978–Herve des Abbayes et al. "Double Carbonylation of Substituted Benzyl Chlorides with Cobalt Carbonyl Anion by Phase Transfer Catalysis to Give Arylpyruvic Acids", pp. 1090–1091.

*Primary Examiner*—Paul J. Killos
*Attorney, Agent, or Firm*—Karl W. Flocks; Sheridan Neimark

[57] ABSTRACT

The invention concerns a process for preparation of crystallized monohydrated sodium phenylpyruvate comprising: hot reacting benzaldehyde in an aqueous medium in the presence of a catalytic quantity of ethanolamine with the stoichiometric quantity of hydantoin, then treating the reactional medium hot at pH=14 through an excess of sodium hydroxide, acidifying to pH=9 with concentrated hydrochloric acid the so obtained solution and separating the formed precipitate.

2 Claims, No Drawings

PROCESS FOR PREPARATION OF CRYSTALLIZED MONOHYDRATED SODIUM PHENYLPYRUVATE

This invention relates to a process for preparation of 2-oxo-3-phenyl sodium propionate crystallized with one molecule of water hereinafter designated as crystallized monohydrated sodium phenylpyruvate. This salt is a precious raw material for preparing phenylalanine.

Crystallized monohydrated sodium phenylpyruvate is known. It has been obtained among others by R. HEMMERLE upon hydrolysis of éthyl-3-cyano-2-oxo-3-phenyl-propionate (Annales de Chimie et de Physique, 1917, (9) 7, 226-276). There is also known to prepare it by hydrolyzing 5-benzylidene hydantoin (B. A. IVIN et al.Zhur.org.Khim. 1977 13 (9), 1970-80) from the condensation of benzaldehyde over hydantoin (H. L. WHEELER et al. Amer.Chem.J. 1911,45 369; W. J. BOYD, Biochem.J. 1935, 29, 542-5; The DOW CHEMICAL Co., U.S. Pat. No. 2,861,079; DEGUSSA A. G., European Patent Application Nos. 0 037 479 and 0 037 480, French Patent Application No. 2,485,011). Analysis of such documents shows that to accede at the sodium phenyl pyruvate crystallized with one molecule of water from benzaldehyde and hydantoin in the presence of a catalyst such as ammonium acetate or the alkanol amines, it is necessary to achieve such synthesis in two steps, with isolation of the intermediary 5-benzylidene hydantoin. Industrially, this method is therefore little economic and other synthesis methods were tried such as carbonylation of benzyl halides(MONTEDISON S.p.A. U.S. Pat. No. 4,351,952; RHONE POULENC S.A. French Patent Application No. 2,297,200).

However, the Applicant has surprisingly discovered that sodium pyruvate crystallized pure with one molecule of solvatation water having an excellent yield can be obtained in one step starting from benzaldehyde and hydantoin.

The process according to this invention is the more surprising because it is rapid, little expensive and of easy implementation.

The process according to this invention is characterized by heating with reflux for several hours an aqueous equimolecular suspension of benzaldehyde and hydantoin in the presence of a catalytic quantity of ethanolamine, continuing with the reflux for several tens of minutes at pH=14 after addition of an excess of sodium hydroxyde into the reactional medium, then acidifying the obtained solution cooled to the ambient temperature at pH=9, with concentrated hydrochloric acid, then squeezing and washing by impasting with iced water the so obtained crystallized product and finally, drying under vacuum at 60° C. at constant weight.

Advantageously, the process according to this invention is carried out by heating for four hours with reflux a suspension consisting of one mole of benzaldehyde, one mole of hydantoin and 0.1 mole of ethanolamine in 240 g of permuted water, then continuing the reflux for 30 minutes in the presence of 1000 cm³ of 5N sodium hydroxyde, by acidifying thereafter the obtained solution previously cooled to the ambient temperature at pH=9, with concentrated hydrochloric acid, squeezing and then washing by impasting with iced water the formed precipitate and finally, drying at constant weight under vacuum at 60° C. Thus, there is obtained sodium phenylpyruvate crystallized pure with one molecule of solvatation water with excellent yield higher than 75% of the theoretical value.

As previously mentioned, sodium phenylpyruvate crystallized with one molecule of water submitted to a reducing amination reaction leads to phenylalanine. (UNITIKA Ltd. Japanese Patent Application No. 52(77)-48601).

The following Example illustrates this invention without however any limitation thereof:

EXAMPLE 1

There is heated for 4 hours with reflux under agitation and in an inert atmosphere:

106 g (1 mole) of benzaldehyde,
100 g (1 mole) of hydantoin,
6.1 g (0.1 mole) of ethanolamine in 240 g of permuted water.

During the reflux the reactional medium passes into solution, then again provides a suspension.

Thereafter, there is introduced 1000 cm³ of 5N sodium hydroxyde ie. 5 moles of sodium hydroxide, then the reflux is continued for 30 minutes. The obtained solution is then cooled to the ambient temperature, and thereafter it is brought to pH=9 through addition thereto of concentrated hydrochloric acid. The desired product crystallizes slowly; the precipitate is left to mature for 24 hours, then it is squeezed and thereafter it is washed by impasting with one volume of iced water. Thus, there is obtained after drying at constant weight at 60° C. under vacuum a first quantity of 153.1 g (0.75 mole) of sodium phenylpyruvate crystallized with one molecule of water colourless and homogeneous upon thin layer chromatography.

Through concentration of mother waters there is isolated a second quantity of 28.5 g (0.14 mole) of sodium phenylpyruvate crystallized with one molecule of water, colourless and homogeneous upon thin layer chromatography.

The overall yield is determined to 99% of the theoretical value.

| $C_9H_7NaO_3, H_2O$ | Microanalysis: C % | H % | $H_2O$ %+ |
|---|---|---|---|
| calculated | 52.94 | 4.44 | 8.8 |
| found | 52.8 | 4.4 | 9.3 |

+as determined by Karl Fischer.

It will be understood that this invention was only described in a purely explanatory and not at all limitative manner and that any useful modification thereof can be effected without however departing from its scope as defined in the appended claims.

We claim:

1. A process for preparation of crystallized monohydrated sodium phenylpyruvate comprising: hot reacting benzaldehyde in an aqueous medium in the presence of a catalytic quantity of ethanolamine with the stoichiometric quantity of hydantoin, then treating the reactional medium hot at pH=14 through an excess of sodium hydroxide, acidifying to pH=9 with concentrated hydrochloric acid the so obtained solution and separating the formed precipitate.

2. A process according to claim 1, comprising after treatment with sodium hydroxide and hydrochloric acid, squeezing the formed precipitate, washing with iced water, and finally, drying at constant weight under vacuum at 60° C.

* * * * *